(12) United States Patent
Scholz

(10) Patent No.: US 7,850,969 B2
(45) Date of Patent: Dec. 14, 2010

(54) LEUKOCYTE INACTIVATION MODULE

(75) Inventor: Martin Scholz, Frankfurt (DE)

(73) Assignee: Leukocare GmbH, Munich (DE)

( * ) Notice: Subject to any disclaimer, the term of this patent is extended or adjusted under 35 U.S.C. 154(b) by 0 days.

(21) Appl. No.: 12/114,349

(22) Filed: May 2, 2008

(65) Prior Publication Data

US 2008/0292643 A1  Nov. 27, 2008

Related U.S. Application Data

(63) Continuation of application No. 10/489,831, filed on Sep. 16, 2002, now abandoned.

(30) Foreign Application Priority Data

Sep. 27, 2001 (DE) ................................ 101 47 638

(51) Int. Cl.
*A61K 39/44* (2006.01)
*B01D 24/00* (2006.01)
*A61M 1/06* (2006.01)
*A61M 1/34* (2006.01)

(52) U.S. Cl. .............. 424/143.1; 424/172.1; 424/178.1; 435/7.1; 435/7.24; 210/323.1; 604/6.03

(58) Field of Classification Search ........................ None
See application file for complete search history.

(56) References Cited

U.S. PATENT DOCUMENTS

| 5,639,376 A | 6/1997 | Lee et al. |
| 5,840,083 A | 11/1998 | Braach-Maksvytis |
| 6,204,055 B1 | 3/2001 | Dean et al. |
| 6,797,514 B2 | 9/2004 | Berenson et al. |

FOREIGN PATENT DOCUMENTS

| DE | 691 19 683 | 7/1990 |
| DE | 10147638 | 4/2003 |
| EP | 1 010 428 | 6/2000 |
| WO | 9518665 | 7/1995 |
| WO | 9712632 | 4/1997 |
| WO | 9738707 | 10/1997 |
| WO | 9846242 | 10/1998 |

OTHER PUBLICATIONS

Watson R. W. G. et al., "Regulation of Fas antibody induced neutrophil apoptosis is both caspase and mitochondrial dependent" FEBS Letters, Elsevier Science Publishers, Amsterdam, NL, vol. 453, No. 1-2, Jun. 18, 1999, pp. 67-71.
Cinatl J Jr et al., "Decreased neutrophil adhesion to human cytomegalovirus-infected retinal pigment epithelial cells is mediated by virus-induced up-regulation of Fas ligand independent of neutrophil apoptosis." Journal of Immunology (Baltimore, MD.: 1950) United States Oct. 15, 2000, vol. 165, No. 8, pp. 4405-4413.
R. William G. Watson, et al., "Regulation of Fas antibody induced neutrophil apoptosis is both caspase and mitochondrial dependent" FEBS Letters, vol. 453, No. 1-2, pp. 67-71, Jun. 18, 1999.
Francois et al, Biomaterials 17:667-678, 1996.
Jindrich Cinatl. Jr., et al., "Decreased neutrophil adhesion to human cytomegalovirus-infected retinal pigment epithelial cells is mediated by virus-induced up-regulation of Fas ligand independent of neutrophil apoptosis" Journal of Immunology, vol. 165, No. 8, pp. 4405-4413, Oct. 15, 2000.
Desbarats et al, Proc natl. Acad Sci USA 93:11014-11018, Oct. 1996.
Garrone et al, J Exp Med 182: 1265-1273, 1995.
Hata et al, Leukemia & Lymphoma 24(1-2): 35-42, Dec. 1996.
Stryer et al, in Biochemistry, Third edition, W H Freeman Company, New York, pp. 31-33, 1998.
Yoshida-Kato et al, Biosci Biotechnol. Biochem 64(9): 1903-1908, 2000.
Rudikoff et al, Proc Natl Acad Sci USA 1982 vol. 79, p. 1979.
Kobrin et al, J. Immunology 146:2017-2020, 1991.
Barrios et al, J. Molecular Recognition 17: 332-338, 2004.

*Primary Examiner*—Phuong Huynh
(74) *Attorney, Agent, or Firm*—Oblon, Spivak, McClelland, Maier & Neustadt, L.L.P.

(57) ABSTRACT

The present invention provides a module for reducing the activity of leukocytes which comprises a carrier and a ligand that is linked to the carrier and is suitable for interacting with a leukocyte receptor. Furthermore, the present invention provides a process for reducing the activity of leukocytes using said module. The advantage of the present invention is that after binding the activated leukocytes in the leukocyte inactivation module (LIM), the damaging effect of the cells is inhibited within minutes.

7 Claims, 1 Drawing Sheet

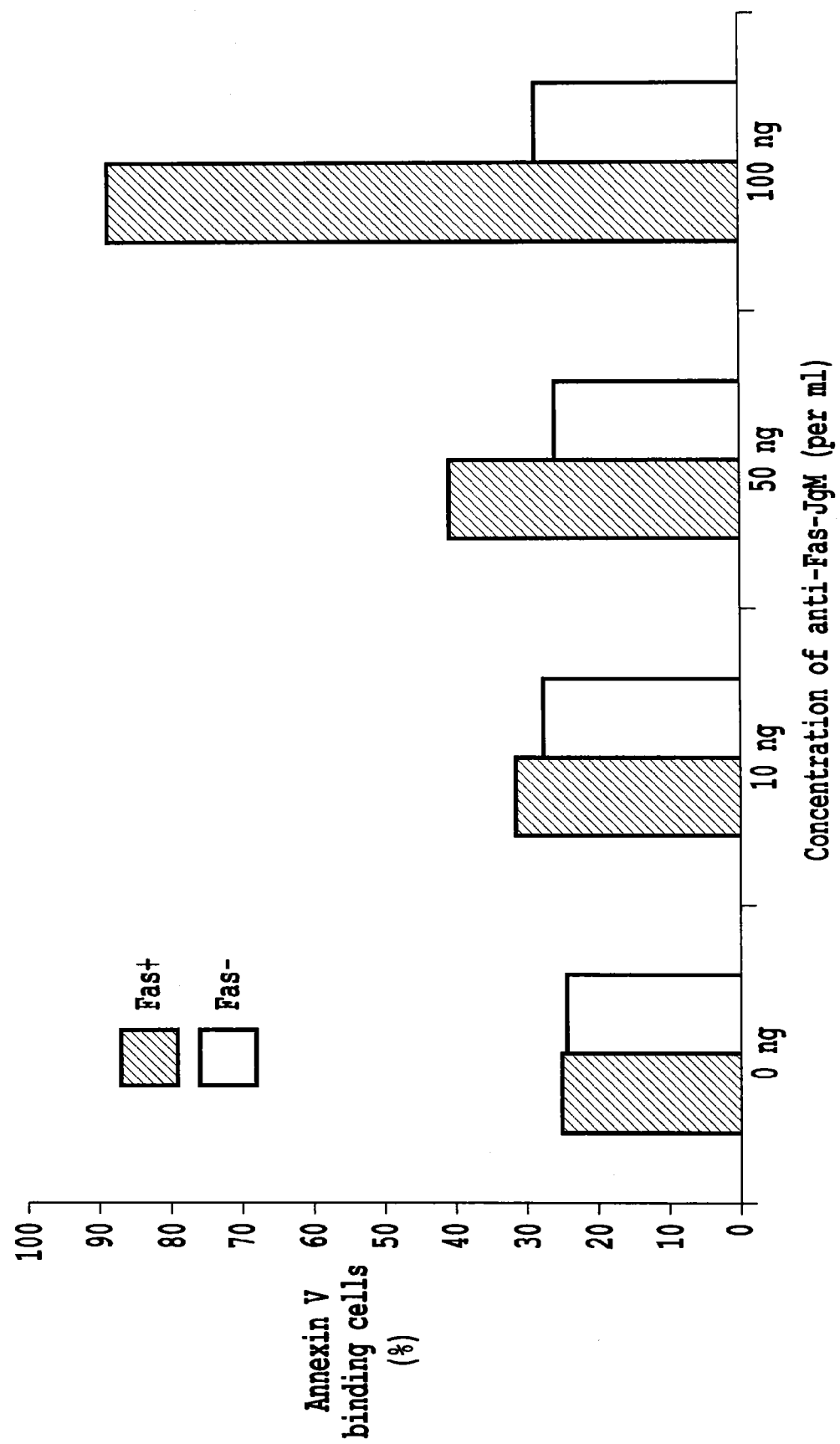

LEUKOCYTE INACTIVATION MODULE

CROSS-REFERENCE TO RELATED APPLICATIONS

This application is a continuation of U.S. Ser. No. 10/489,831, abandoned, which was a 371 of PCT/DE02/03466 filed Sep. 16, 2002.

FIELD OF THE INVENTION

The present invention relates to a leukocyte inactivation module (LIM) and a process for reducing the activity of leukocytes.

BACKGROUND OF THE INVENTION

An acutely increased pathologic cellular immune response frequently occurs in various clinical situations. Examples therefore are:

The arterial or venous line of a heart-lung-machine during cardiosurgery;

Systemic Immune Response Syndrome (SIRS) after multiple injuries or sepsis (septic shock);

Multiple Organ Dysfunction Syndrome (MODS) due to excessive immune activity.

During the above-mentioned surgeries or clinical complications, an undesired activation of leukocytes occurs resulting in severe pathological complications in the patient. To avoid this, the activated leukocytes (in particular, neutrophils) should be removed from the blood stream and inactivated immediately. In the currently available leukocyte filters, an increased number of activated leukocytes are filtered off from the blood. However, the cells still living produce and secrete pathogenic substances (cytokines, enzymes, oxygen radicals etc.) that are responsible for the actual pathogenesis. There are indications that the leukocytes in the filter net are additionally activated presumably through mechanical stress und through the contact of the cells with the foreign surface. As an example, the enzyme elastase produced by activated neutrophils is secreted in a higher amount. Elastase acts inter alia on the extracellular matrix of the vessel wall and cleaves inter-endothelial cell-cell contacts resulting in an increased permeability of the vessel walls, in edema, in enhanced inflammation and the like.

Apoptosis is one of the most important regulation elements of the immune system. The apoptosis of immunrelevant cells results in a normalisation of the activity of the immune system after an immune response, e.g. against microbial pathogens. Also during the individual development, the immune system must kill those immune cells acting on endogenous structures or on natural antigens from the environment (e.g. autoimmune diseases or allergies). T-cells being activated via so-called antigen-presenting cells (apc) usually receive several pieces of information. The antigen processed by the apc is presented in the group of the MHC-I or MHC-II molecule. If the affinity of the T-cell receptor to the antigen is too weak or in the absence of co-stimulating signals (e.g. via adhesion molecules), the cell becomes apoptotic. Another essential mechanism resulting in apoptosis is started via the Fas/FasL pathway. In this mechanism, e.g. endothelial cells of the vessel walls or other epithelial cells can express FasL thus protecting the tissue from entering activated immune cells.

PROBLEM TO BE SOLVED BY THE INVENTION

It is the aim of the present invention to provide a device suitable for reducing the activity of leukocytes, thereby reducing the secretion of pathogenic substances by the leukocytes. Furthermore, the present invention is to provide a process for reducing the activity of leukocytes using such device.

MEANS FOR SOLVING THE PROBLEM

The present inventors carried out investigations with cytomegalovirus-infected retinal pigment epithelial cells from the human eye and found that, due to the contact with FasL on the epithelial cells, activated neutrophils lost their ability to maintain or increase the adhesion to the epithelial cells. This surprising result is supposed to be a protecting mechanism of the endothelium and the respective tissue against inflammatory incidents. The functional loss of the neutrophil-effector-mechanisms could be observed within minutes after cell-cell contact and seems to be largely independent of the apoptotic signal pathway in the neutrophils. On the basis of these surprising findings, e.g. the Fas/FasL pathway or other early inhibitory mechanisms of the leukocyte-effector functions can be employed for the experimental and clinical use for acute excessive immune reactions.

SUBJECT-MATTER OF THE INVENTION

The present invention provides a module for reducing the activity of leukocytes, which comprises a carrier and a ligand that is linked to the carrier and is suitable for interacting with a leukocyte receptor. Furthermore, the present invention provides a process for reducing the activity of leukocytes using said module.

The advantage of the present invention is that after binding the activated leukocytes in the leukocyte inactivation module (LIM), the damaging activity of the cells is inhibited within minutes. This is due to the contact of specific receptors on the cell membrane of the leukocytes with the respective ligands in the LIM. The ligands can be proteins inducing, after contact with the receptor on the cell membrane, a signal that stimulates leukocytes to reduce the secretory activity and the immunogenicity. A possibility to achieve this is the induction of apoptosis via relevant receptor-ligand interactions, e.g. Fas/FasL.

DESCRIPTION OF THE INVENTION

The module according to the present invention is suitable for being introduced into the patient's blood stream using a Shaldon catheter or into the circulation of a heart-lung machine.

The module preferably consists of a plastic housing with a diameter of e.g. 10 cm. The blood inlet nozzle and the blood outlet nozzle are adapted to the tube connections of the heart-lung machine. There is a carrier in the module, e.g. a three dimensionally folded polyester membrane with modified surface for the adhesion of activated leukocytes and for their inactivation and killing (e.g. induction of apoptosis) via receptor-induced signals. The carrier material can be any material that is suitable for binding ligands. The term "binding" used herein comprises both covalent and non-covalent binding, e.g. salt binding, hydrophobic interactions and affinity binding, of a ligand to the carrier. Furthermore, the ligand may be bound directly or indirectly to the carrier. The indirect binding comprises binding via a binding mediator, e.g. a long-chain molecule, for a better presentation of the ligand or via a cell comprising the ligand and being bound to the carrier via another binding interaction.

The LIM according to the present invention is suitable for any leukocytes, i.e. for B-lymphocytes, T-lymphocytes, granulocytes, neutrophils.

The other parameters of the module determining the blood stream, pressure or rheology are the same as in conventional leukocyte filters that are already used clinically.

EXAMPLE 1

The wells of a 12-well culture plate were lined with polyester membranes (pore size of 40 μm) and incubated overnight with various concentrations of a functionally activated IgM antibody against Fas (CD95). The following controls were used:

wells without membrane wells with membrane, no pre-incubation with antibody was carried out wells with membrane, pre-incubation with irrelevant IgM antibodies was carried out.

Fas-expressing (Fas+) and Fas-deleted (Fas−; expresses no Fas on the surface) Jurkat cells as test cells were added to the wells in a concentration of $1\times10^6$/ml for 24 hours.

The apoptosis rate and the necrosis rate were determined quantitatively by flow cytometry using an annexin binding assay.

Results: The Fas-Jurkat cells showed no significant increase in the annexin V binding property after cultivation in the pre-treated wells. In contrast thereto, a significant induction of apoptosis showed in dependency on the concentration of the IgM antibody.

|        | Fas+    | Fas−               |
|--------|---------|--------------------|
| 0 ng   | 24.81%  | 24.29% (control value) |
| 10 ng  | 31.38%  | 27.57%             |
| 50 ng  | 40.95%  | 26.20%             |
| 100 ng | 89.31%  | 29.65%             |

In the above controls, no induction of apoptosis could be found. Similar results were obtained with freshly isolated neutrophils.

FIG. 1 shows the results of the example of the present invention.

The invention claimed is:

1. A module for reducing the secretory activity of leukocytes, which comprises a plastic housing, a carrier in the module, a blood inlet nozzle, a blood outlet nozzle; and an antibody against Fas (CD95) that is linked to the carrier via covalent or non-covalent binding.

2. The module according to claim 1, wherein the antibody is linked to a binding mediator that is linked to the carrier.

3. The module according to claim 2, wherein the binding mediator is a cell.

4. The module according to claim 1, wherein the carrier comprises a three dimensionally folded polyester membrane with a modified surface for adhesion of activated leukocytes and for inactivation and killing of leukocytes via receptor-induced signals.

5. A process for reducing the secretory activity of leukocytes in blood, comprising introducing the blood through the blood inlet nozzle of the module of claim 1 whereby the leukocytes in the blood contact the antibody linked to the carrier such that the activity of the leukocytes in the blood is reduced.

6. The process according to claim 5, wherein the leukocytes, after contacting with the antibody, secrete at least one of cytokines, enzymes, and oxygen radicals in lower amount than before contacting.

7. The process according to claim 5 or 6, wherein the interaction of the antibody to the leukocyte reduces the activity of the leukocytes in terms of binding affinity to a cell.

* * * * *